United States Patent [19]

Simmonds et al.

[11] Patent Number: 4,520,109

[45] Date of Patent: May 28, 1985

[54] FLUOROCARBON TRACERS AND TRACING METHOD

[75] Inventors: Peter G. Simmonds, Ringwood, England; Robert E. Moore, Wilmington, Del.

[73] Assignee: Sun Tech, Inc., Philadelphia, Pa.

[21] Appl. No.: 475,001

[22] Filed: Mar. 14, 1983

[51] Int. Cl.$^3$ .................... G01N 33/28; G01N 31/08
[52] U.S. Cl. ........................................ 436/56; 436/27; 436/126
[58] Field of Search ................... 436/27–31, 436/56, 124–126; 128/632, 654

[56] References Cited

U.S. PATENT DOCUMENTS

| | | | |
|---|---|---|---|
| 3,931,143 | 1/1976 | MacLeay et al. | 526/330 X |
| 4,105,798 | 8/1978 | Moore et al. | 424/352 |
| 4,256,038 | 3/1981 | Dietz et al. | 102/28 R |

OTHER PUBLICATIONS

Exotic Tracers for Atmos. Studies; Lovelock et al., Atmos. Envir. vol. 16, No. 6, pp. 1467–1471, 6/8/82.
Perfluoro Carbons as Hydrological Tracers; Kerrin 2/25/81.

*Primary Examiner*—Barry S. Richman
*Assistant Examiner*—Michael S. Gzybowski
*Attorney, Agent, or Firm*—J. Edward Hess; Donald R. Johnson; Stanford M. Back

[57] ABSTRACT

A material is traced to its origin or the flow pattern of a fluid medium is defined by incorporating into the material or fluid medium a perfluorinated $C_9$–$C_{18}$ polycyclic hydrocarbon containing at least two bridgehead carbon atoms linked through a bridge containing at least one carbon atom, collecting a sample of the material or fluid medium after distribution or flow, and analyzing the sample for the presence of the perfluoro compound.

10 Claims, No Drawings

FLUOROCARBON TRACERS AND TRACING METHOD

BACKGROUND OF THE INVENTION

This invention relates to chemical tracing, more particularly to the incorporation of detectable fluorine compounds into materials or a fluid medium such that the materials can be identified and distinguished from materials from other sources or such that the flow pattern of the fluid medium can be defined.

A considerable technology has developed in recent years for the identification of materials or for studying the flow patterns of fluid media. For example, U.S. Pat. No. 3,964,294 to Shair et al describes the microencapsulation of analyzable compounds not normally present in petroleum crude oil and refined liquid products thereof, the incorporation of the microcapsules in the oil or liquid products, the sampling of the oil or liquid products containing the microcapsules at some location removed from the point of origin, and the analysis of the encapsulated substance by electron capture gas chromatography. In this manner the origin of the oil containing the microcapsules can be determined based upon a preestablished code or identification of the analyzable substance with a particular source of the oil or refined liquid product. The chemical tracers in such applications are termed "taggants" since they are used to label, code or "tag" the material to be identified. In this specification, "tracing" is used as a general term; taggants are one species of tracers.

The advantage of the encapsulation is that it overcomes problems associated with injecting chemical tracers directly into a material or fluid, whose movement or flow pattern is to be traced. These problems include incompatibility of some tracers with the material or fluid to be traced, interference by or confusion with other substances in the material or fluid (such as substances having a similar chemical composition), and possible contamination of the tracers with particulate matter such as spores, pollens or other microbial substances or precipitants which interfere with or complicate the separation and characterization of the tracers.

Nevertheless, even assuming the effectiveness of the encapsulation for solving the foregoing problems, the tracer material itself must have certain characteristics for efficacy. These include unique chemical composition so that its detection profile (for example, chromatographic pattern) is associated only with the tracer, a high degree of detectability (of the order of about 1 part in $10^6$ to $10^{12}$ parts by volume) by available detection systems, and sufficient inertness so that the tracer is not lost due to chemical, physical or biological interactions which may be encountered in use.

Chemical inertness is especially critical when a catalytic reactor is used preliminary to electron capture detection to convert substances in the sample, other than the tracer, to products which will not interfere with the analysis. For example, it is common practice to employ a palladium catalyst reactor "clean up" system prior to electron capture gas chromatography to remove certain halogenated hydrocarbon contaminates present in the atmosphere by converting the contaminates to elemental hydrides or other non-interfering products.

Applications and embodiments of material or flow pattern tracers are described in the literature, including detection techniques. In addition to U.S. Pat. No. 3,964,294 mentioned above, the following publications are representative of the literature on this subject: P. G. Simmonds et al., "Continuous and Ultra Sensitive Apparatus for the Measurement of Air-borne Tracer Substances", *Journal of Chromatography*, 126 (1976), pages 3-9, describing an electron capture detector apparatus, and incorporating a reference to gas chromatography ("GC") coupled with an electron capture detector ("ECD" or "EC detector"); U.S. Pat. No. 4,304,752 describing an ECD apparatus for detection of a tracer material in the atmosphere; U.S. Pat. No. 4,256,038 describing a palladium reactor in combination with ECD and GC for the detection of perfluorocarbon taggants in blasting cap detonators; U.S. Pat. No. 4,141,692 describing ECD/GC detection of taggants in fuel compositions; and U.S. Pat. No. 3,585,845 describing ECD for detection of leaks of a gaseous substance from a vessel or pipeline, based upon the presence of a tracer gas in the gaseous material. Representative U.S. patents describing the use of tracers in other applications but not necessarily involving ECD are the following: U.S. Pat. No. 4,303,411 describing the use of fluorocarbons in oil field tracing, using $^{19}$FNMR spectroscopy; U.S. Pat. No. 4,299,709 describing tracer fluids for enhanced oil recovery, utilizing standard chemical analytical procedures; and U.S. Pat. No. 2,445,494 describing a method of determining the fluid content (gas, oil and water) of a formation or a core sample therefrom, wherein the contamination of the samples by drilling fluids is traced by incorporation of a tracer material into the drilling fluids.

As evident from the foregoing literature, fluorine compounds, and in particular perfluoro compounds, generally have the inertness and structural uniqueness required for use as tracers. Nevertheless, many perfluoro compounds decompose when it is necessary to catalytically treat a sample containing the perfluoro compound tracer for the purpose of eliminating contaminants prior to analysis to confirm the presence of the tracer material.

SUMMARY OF THE INVENTION

In accordance with the present invention a new class of perfluorocarbons (hereinafter sometimes referred to as "PFC's") is identified for use as chemical tracers which not only satisfies the aforementioned requirements for unique chemical composition, high degree of detectability and solubility characteristics which permit formulation of the tracer with dispersing aids such as surfactants, but also exhibits a degree of chemical inertness enabling the tracer to survive, substantially intact, on passage through a heated catalytic reaction chamber sometimes used preliminary to analysis, for example by ECD alone or in combination with GC.

The class of taggants having the foregoing characteristics are perfluorinated $C_9$–$C_{18}$ polycyclic hydrocarbons such as F-adamantane and like compounds.

In one aspect of the invention, a material is identified and traced to its origin by incorporating in the material a detectable amount of a taggant comprising a perfluorinated $C_9$–$C_{18}$ polycyclic hydrocarbon, permitting distribution of the material, collecting a sample of the material, and analyzing the sample for the presence of the taggant. Practical applications of this aspect include the coded tagging of ethical drugs, explosives, ammunition, petroleum crude oil and refined liquid products thereof, such as described in the aforementioned U.S.

Pat. Nos. 3,964,294, 4,141,692 and 4,256,038, wherein the objective, for example, is to police the distribution of certain materials or to detect the origin of a contamination such as an oil spill.

In another aspect, the flow patterns of a fluid medium are traced by providing in the fluid medium a perfluorinated $C_9$–$C_{18}$ polycyclic hydrocarbon of the invention, collecting a sample of the fluid medium containing the PFC at one or more locations during or after flow, and analyzing the sample for the presence of the PFC. Significant details of the operation of this aspect of the invention are set forth in the literature such as the aforementioned U.S. Pat. Nos. 4,299,709, 4,304,752 and 4,303,411. More generally, this aspect of the invention may be practiced in connection with tracing the flow and source of atmospheric pollution, hydrologic tracing such as studies on the age and flow patterns of ground waters and leakage of fluids from waste disposal ponds, determination of the flow patterns and content of industrial emissions, mapping of petroleum formations and flow patterns, tracing of sewage effluent discharge, meteorological and oceanographic tracing, geochemical prospecting, and biological tracing as in studies on flow patterns and pressures exerted by body fluids.

It will be evident from the specification following that the invention can be practiced in conjunction with any environments wherein a purpose is to identify the origin of a material or to define the flow pattern of a fluid medium.

DETAILED DESCRIPTION

The unique tracers used in this invention comprise perfluorinated $C_9$–$C_{18}$ polycyclic hydrocarbons containing at least two bridgehead carbon atoms linked through a bridge containing at least one carbon atom. These perfluoro compounds are described in the prior art such as in U.S. Pat. Nos. 3,641,167 to R. E. Moore and E. J. Janoski and 4,105,798 to R. E. Moore and L. C. Clark, Jr. By way of summary but not limitation, the compounds are non-aromatizable, polycyclic perfluorocarbons having two bridgehead carbon atoms linked through a bridge containing at least one carbon atom. Preferably, the polycyclic compounds contain 9–12 carbon atoms and generally will have not more than four rings, usually two or three rings. By "non-aromatizable" is meant incapability of aromatization of the ring structure of the compounds without destruction of the original carbon to carbon cyclic bonds. This distinguishes the perfluoro compounds of the invention from perfluoro multi-ring compounds such as perfluorodecalin or similar compounds which can be aromatized.

"Perfluoro compound" or "perfluorocarbon" as used herein refers to a substantially fluorinated or completely fluorinated material which is generally but not necessarily a liquid at ambient temperature and pressure. Those fluorinated compounds which are solids under ambient conditions can nevertheless be rendered useful in the invention by encapsulation, as described below, by dissolution in a suitable solvent, or by emulsification or dispersion in a suitable medium, also as described below. "Substantially fluorinated" as used herein means that most of the hydrogen atoms of the compound have been replaced by fluorine atoms of the order of at least about 80–90%. However, it is preferred that at least 95% of the hydrogen atoms have been replaced, more preferably at least 98% and most preferably, 100%.

Representative compounds of the invention are the perfluoroderivatives of such $C_9$–$C_{18}$ polycyclic compounds as bicyclononanes (e.g. bicyclo[3.3.1.]nonane, 2,6-dimethylbicyclo [3.3.1.]nonane, 3-methylbicyclo[3.3.1.]nonane and trimethylbicyclo[3.3.1.]nonane), adamantane and alkyl ($C_1$–$C_6$) adamantanes such as methyl and dimethyladamantane, trimethyladamantane, ethyl and diethyladamantane, trimethyl and triethyladamantane, ethylmethyladamantane, ethyldimethyladamantane; tetrahydrodicyclopentadiene, bicyclo[2.2.1.]octane, methyl and dimethylbicyclooctane, tetrahydrobinor-S, methyldiadamantane, trimethyldiadamantane, ethyldimethyldiadamantane, pinane, camphane, 1,4,6,9-dimethanodecalin, bicyclo[4.3.2.]undecane, tricyclo[5.2.1.0.$^{2,6}$]decane, methyltricyclo[5.2.1.0.$^{2,6}$]decane, and the like, or mixtures of any two or more thereof such as mixtures of dimethyladamantane and trimethylbicyclononane, ranging from about 90/10 to 10/90 by weight.

The more preferred perfluoro compounds for use in the invention on the basis of relative inertness (chemical and biological) and good dispersability are the perfluoro $C_9$–$C_{18}$ polycyclic hydrocarbons of U.S. Pat. No. 4,105,798, and particularly, F-adamantane, F-methyladamantane, F-dimethyladamantane, F-trimethylbicyclonane, F-tricyclo[5.2.1.0.$^{2,6}$]decane, F-methyltricyclo[5.2.1.0.$^{2,6}$]decane and 1-hydropentadecafluorotricyclo[5.2.1.0.$^{2,6}$]decane, including any isomers thereof, and mixtures of such compounds, for example, mixtures of F-alkyladamantanes and F-alkylbicyclononanes such as 50/50 mixtures of F-dimethyladamantane and F-trimethylbicyclononane.

Techniques are well known for producing the perfluoro polycyclic compounds of the invention, as described in U.S. Pat. Nos. 4,105,798, 4,041,086 and 4,220,606.

In some tracing applications it may be desirable first to admix, disperse, dissolve or emulsify the perfluoro compound in a liquid medium so that the perfluoro compound will remain in the material or fluid medium being traced. For example, the tracing of oil spills by introducing the perfluoro compound directly into the petroleum requires that the perfluoro compound have sufficient solubility in the oil phase so that it will be present when detection is undertaken. If the compound is not itself sufficiently soluble, it can be solubilized by emulsification or other dispersion technique. A similar requirement exists when tagging fuel compositions: the taggant should be soluble or otherwise dispersible in the fuel, such as described in U.S. Pat. No. 4,141,692. In such cases no prior emulsificaton or other dispersion of the perfluoro compound is required, although dissolving in a hydrocarbon solvent may sometimes be useful. But in tracing flows and formation conditions when using water flooding for enhanced oil recovery, such as described in U.S. Pat. Nos. 4,299,709 and 4,303,411, the tracer must be rendered water soluble or at least water dispersible so that it will be carried by the aqueous fluid injected. Similarly, the determination of flow patterns or the tracing of contaminated streams and ground water may require blending the perfluoro compound with a water solubilizing compound such as a water soluble alcohol, or even emulsifying the perfluoro compound in water with a suitable surfactant.

The preferred dispersants for uniformly dispersing the perfluoro compounds in an aqueous medium are the nonionic surfactants because such surfactants normally are compatible with any fluid medium or environment. Ionic or amphoteric surfactants may also be used in those cases where the fluid medium or environment under study is compatible with such surfactants, e.g., contain no electrolytes which would react with the surfactants, thereby breaking the emulsions or causing coagulation or other interference.

Suitable nonionic surfactants include aliphatic materials such as block copolymers of ethylene oxide and propylene oxide comprising a hydrophobic propylene oxide section combined with one or more hydrophilic ethylene oxide sections, for example the "Pluronic" (trademark) surfactants available from BASF-wyandotte, Inc. Aromatic types may also be used, such as alkylphenoxypolyethyoxyethanols having alkyl groups of about 7 to 18 carbon atoms and 1 to 60 or more oxyethylene units, for example: heptylphenoxypolyethoxyethanols, octylphenoxypolyethyoxyethanols, methyloctylphenoxypolyethoxyethanols, nonylphenoxypolyethoxyethanols, dodecylphenoxypolyethoxyethanols, and the like; polyethoxyethanol derivatives of methylene linked alkylphenols; sulfur-containing analogs of the foregoing; ethylene oxide derivatives of long-chain carboxylic acids, such as lauric, myristic, palmitic, oleic, and the like, or mixtures of acids such as are found in tall oil, containing 1 to 60 oxyethylene units per molecule; and analogous ethylene oxide condensates of long-chain or branched-chain amines, such as dodecylamine, hexadecylamine, and octadecylamine, containing 1 to 60 oxyethylene groups.

Naturally occurring emulsifiers or derivatives thereof are also useful. These include the alginates, cellulose derivatives such as methyl cellulose and carboxymethyl cellulose, water soluble gums such as gum arabic and gum tragacanth, the phospholipids (such as lecithin and yolk phospholipid), and the sterols.

Nonionic fluorine containing surfactants are particularly preferred. The fluorinated alkyl esters available from 3M Company are one class, having the designations FC-93, FC-95, FC-128, FC-143, FC-430 and FC-431. Another class of fluorine containing surfactants are the fluorinated amidoamine oxides described in U.S. Pat. Nos. 3,828,085 to Price et al. and 3,547,995 to Bartlett. These surfactants have exceptional ability to form dispersions with the perfluoro compounds and to maintain a range of small particle size over substantial periods of time, of the order of 35 weeks to a year or more, even at room temperature.

Preferred subclasses of the fluorinated amidoamine oxide surfactants of the foregoing patents are those of the following formulas (1) and (2):

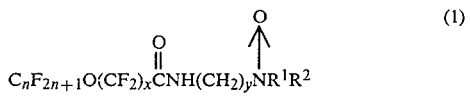
(1)

wherein n is at least 3 (preferably 3-10), x is at least 2 (preferably 2-6), y is at least 1 (preferably 2-6), and $R^1$ and $R^2$ independently are alkyl radicals containing 1-6 carbon atoms.

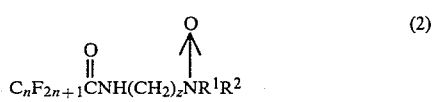
(2)

wherein n is at least 1 (preferably 3-10), z is at least 1 (preferably 2-6), and $R^1$ and $R^2$ independently are alkyl radicals containing 1-6 carbon atoms.

Specific amidoamine oxides within the scope of the above formulas are the products described in Examples 1-6 of U.S. Pat. No. 3,828,085, such as:

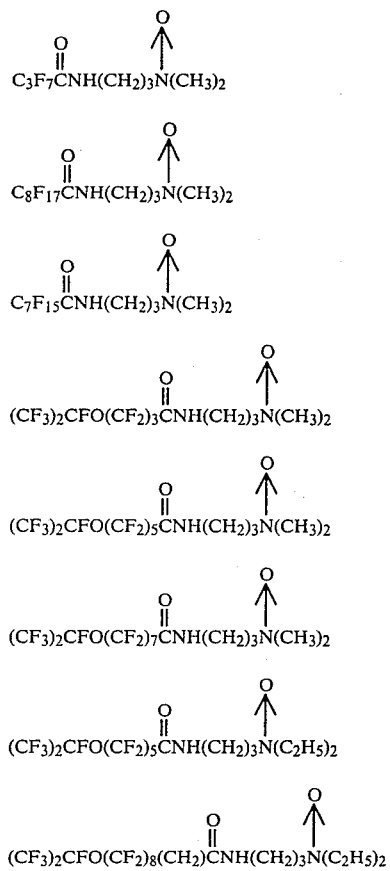

The aqueous dispersions may be prepared by any mixing technique which will provide a uniform blend of the ingredients. In one preparative technique the surfactant is mixed with the water under suitable agitation followed by introduction of the PFC. Since the perfluoro compound is extremely hydrophobic, high energy mixing normally must be employed, such as homogenization or the application of sonic energy.

The perfluoro compound and surfactant components may be blended into water in any proportions which will provide uniform dispersions. Typical proportions are about 5 to 50% perfluoro compound based on the volume of the total composition and about 0.5 to 10% of the surfactant based on the total weight of the composition. Preferred proportions are about 10-30% by volume of the perfluoro compound and about 2-5% by weight of the surfactant, but proportions in particular cases may be varied depending on dispersability of the PFC, particle size desired, and similar considerations.

The aqueous dispersions more usually comprise emulsions, preferably of the oil-in-water type but also including water-in-oil emulsions. In some cases the emulsions have a very fine particle size and appear transparent to the unaided eye. The microemulsions which can be formulated with the dispersants of U.S. Pat. No. 3,828,085 have this characteristic and are preferred. Colloidal suspensions, while not excluded, are less preferred because of their larger particle size range and lower stability.

In practicing the tracing method of the invention, any analytical technique may be employed which provides (1) sufficient selectivity to distinguish the tracer compound from other compounds in the sample, whether such other compounds be solvents used to prepare the samples for analysis, residues of the tagged material or contaminants, and (2) sufficient sensitivity to detect the tracer compound when present in the sample at low concentrations. The combination of conventional gas chromatographic separation and electron capture detection satisfies both requirements and is preferred. Instruments of these types are commercially available from several sources, such a the Hewlett-Packard Corporation, Varian Corporation and Perkin-Elmer Corporation. In those circumstances where separation is not a concern, for example where the sample is relatively pure, such as samples from the atmosphere or from streams where the other components do not interfere with detection of the tracer compounds, the EC detector may be used without GC separation. Real-time, continuous EC detectors have been devised for this purpose, a representative system being that described in the *Journal of Chromatography* article referred to above. Where the sample is impure, it is possible that one component can have a greater electron-capture response than the tracer compound. In these cases GC separation is required and good practice may even suggest pre-analysis using the relatively non-specific flame ionization detector ("FID") to obtain a quick indication of overall sample purity. This preliminary purity data can subsequently be correlated with the GC and ECD analysis to confirm that the major component is in fact the tracer compound.

The EC detector commonly uses a radioactive material such as tritium on titanium or scandium, or nickel 63, as an ionization source and in some cases can be operable up to a temperature of about 350° C. However, since higher temperatures may drive off the ionization source into the carrier gas stream and may damage the detector, lower operating temperatures are preferred. One of the advantages of the tracer compounds of the invention is that they permit optimum detector response at lower temperatures (about 100°–250° C.) and therefore make more practical the development of detectors which are portable and useful in field operations.

GC columns of various sizes and designs may be used for the separations. Suitable columns include a 2.5 meters $\times$ 6.35 mm stainless steel column packed with 10% OV101 silicone on 100–120 mesh Chromasorb P, or with 10% SP210 or OV101 on 100–120 mesh Supelcoport. The columns are maintained isothermally at 30°–50° C. and an inert carrier gas such as argon-methane or nitrogen is flowed through at about 40 ml/min. Such columns will provide sufficient resolution to separate the tracer compounds from most of ubiquitous atmospheric halocarbons such as $CFCl_3$, $CF_2Cl_2$, $CH_3CCl_3$, $CCl_4$ and trichloroethylene or perchloroethylene.

It is sometimes important to pass the sample, prior to GC separation and/or EC detection, through a high temperature catalytic reactor to destroy halocarbon compounds which might co-elute with the tracer and thus interefere with the EC detection. An outstanding advantage of tracer compounds of the invention is a high degree of inertness enabling them largely to withstand this catalytic treatment. Other known compounds, although having good EC detectability, fail in this regard. Typical of such failing compounds are F-amines or ethers, hexafluorobenzene and homologs, F-decalin and homologs thereof, such as F-methyldecalin. In this connection, where it is necessary in preparing samples for analysis to dissolve or disperse the sample in a solvent, solvents should be selected which, if not destroyed by a catalytic treatment, have such low electron affinities as not to significantly interfere with the ECD analysis. High purity alkanes, such as pentane or hexane, and low boiling alcohols such as ethanol or ethanol have this character. Benzene or toluene can also be used as solvents in some cases because they have longer retention times than the perfluorocarbon tracers. High electron absorbing solvents to be avoided are chlorinated hydrocarbons, nitroalkanes and carbon disulfide.

Standard tracer samples for GC/ECD comparison with unknown tracer containing samples, where it is important to determine the concentration of tracer in the unknown sample, are conveniently prepared by dilution of the pure perfluorocarbon, depending on whether the known sample is a gas or a liquid. If the known sample is a gas, serial dilutions or exponential dilutions using a well-mixed exponential dilution chamber are the preferred methods and are well-known in the art.

If the known sample is a liquid, the tracer standards can be prepared by dissolving, for example, about 1–10 microliter volumes (liquid) of the pure tracer in 100 ml. of high purity n-alkanes, such as pentane or hexane. Serial dilutions of these primary standards are then prepared to give a range of concentrations of from about $1 \times 10^{-8}$ to $1 \times 10^{-11}$ gms ml$^{-1}$ or other suitable range. Alternatively, permeation tubes can be used for preparation of perfluorocarbon standards. These tubes are well-known in the art.

The sensitivity of the ECD to any specific tracer compound will, of course, depend on its relative electron-capture efficiency, and solution concentrations should be adjusted to take this effect into account. EC efficiencies are sometimes reported relative to $SF_6$ to $CCl_4$ since these compounds capture one electron per molecule and therefore provide a coulometric response (100% efficiency). Responses relative to these standards of 40% or higher are excellent responses, although lesser responses may be acceptable in some applications. A convenient way to obtain % efficiency readings directly is to employ $SF_6$ or $CCl_4$ standard samples as references while concurrently analyzing the test sample.

Although the PFC tracers of the invention have very low solubilities in almost all solvents, the very high sensitivity of the ECD to them permits their trace detection in almost any medium. Despite the extremely low water solubility of the tracers, aqueous standards can be prepared by vigorously shaking a PFC/water mixture to establish equilibrium and then separating the two phases.

As indicated by the patent and other technical literature cited above, taggant and flow pattern definition uses of fluorine-containing tracer compounds are well established. Whether special shielding of the tracers is required to avoid contamination or loss depends on a number of factors, including the vapor pressure of the tracer relative to the material to be tagged or the fluid whose flow pattern is to be studied. Microencapsulation is one established technique for shielding a tracer material from contamination or from loss due to a vapor pressure higher than the carrier medium. In addition to U.S. Pat. No. 3,964,294 cited above, the article by Mitchell et al in Environmental Science & Technology, 7, 121-124 (February 1973) entitled "Oil Spill Indentification with Microencapsulated Compounds Suitable for Electron Capture" is pertinent in this connection.

Other possible methods of shielding include solvation (hydrocarbons, acetone, and alcohols are most useful), incorporation in other less volatile fluorinated compounds such as Kel-F greases and waxes, and incorporation into closed cell foams. However, where possible it is generally preferable to use the tracers without shielding.

Other tracing applications in which the PFC compounds of the invention will have efficacy are hydrological studies, as described in "Fluorocarbon Tracers In Hydrology," G. M. Thompson et al, Geophys. Res. Letters, 177-180 (1974), and the movement of materials through pipelines as described in the paper by E. R. Adlard et al, "An Apparatus For The Detection of Interfaces Between Products in Pipelines". Because of their inertness and extremely low toxicity, the tracers of the invention will also have utility as biological markers and in tracing fluid movements in animals and plants, similar to the manner in which radioactive tags are used.

The generally high vapor pressures, chemical inertness, nontoxicity, and lack of odor and taste make the PFC tracers of the invention especially useful for atmospheric tracing. Coupled with the fact that instruments are now available which will detect perfluorocarbons in ambient air directly down to one part per trillion by volume, and the capability by concentration techniques to extend the detectivity to less than 1 part in $10^{14}$ parts of air, electron capture detection as used in this invention is probably the most sensitive analytical technique currently available. Furthermore, the method can be made totally specific for perfluorocarbons by passing the tracer sample over a special catalyst of palladised asbestos, or palladised molecular sieve, prior to analysis, to thereby destroy almost all other halocarbons and electron-adsorbing compounds in background air which could act as interference.

In summary, the perfluorocarbon tracers of the invention provide substantial advantages over known fluorine-containing tracers when used either as taggants for identifying the source or distribution of a material or as flow pattern determinants. These advantages include: (1) unique chemical structure and absence in the atmosphere or hydrosphere, making them identifiable even in the presence of contaminants; (2) detectability at very low concentrations by available analytical systems; (3) chemical inertness in various tracer applications, including ability to withstand catalytic clean-up prior to analysis; and (4) capability of being dissolved or dispersed in a test medium, whether aqueous, non-aqueous or gaseous. The perfluoro compounds of the invention are thus outstanding in their ability to operate as tracers in a wide variety of applications.

EXAMPLE 1

The relative detectability of various perfluorinated hydrocarbons of known concentrations was determined, using a Hewlett-Packard Company 5713A gas chromatograph equipped with an electron capture detector. Nickel 63 was the detector ionization source. The chromatographic column was glass, 1.83 m. by 0.635 m. outside diameter, and was packed with 3% OV-1 on 80/100 mesh Chromasorb GHP adsorbent (high performance grade, acid washed and silanized). The carrier gas was a 95/5 argon/methane mixture and carrier gas flow rate was 60 ml./min. Column temperature was 60° C. isothermal. Sample size was 1 microliter. A Hewlett-Packard Company 3385 digital processor was used to record the chromatogram and to determine peak areas. Detector injection port and operating temperature (oven) was 250° C.

Standard solutions of the perfluorocarbons to be analyzed were prepared by dissolving the perfluorocarbon in a high purity paraffinic hydrocarbon and then serially diluting to prepare samples having perfluorocarbon concentrations ranging from 1 part per million (volume), ppm, to 1 part per billion (volume), ppb. Solvents used were nanograde isooctane and n-pentane.

Table I below gives the results of three analytical series as average responses of three determinations on each sample. The average responses include a correction (by subtraction) for the response of the solvent. The solvent in Series A and B was isooctane and in Series C was n-pentane.

It will be seen from the response factors in all of the series that F-dimethyladamantane outranks all other perfluorocarbons in its sensitivity to detection. F-decalin in all of the series exhibits a respectable sensitivity but this compound would decompose if a palladium catalyzed cleanup was used on a sample prior to GC/ECD analysis. The lower sensitivity of F-tetramethyladamantane relative to the excellent sensitivities of the other perfluorocarbons is believed due to the higher degree of methyl substitution in this compound. The limit of detectability in these experiments was found to be 20 parts per billion.

TABLE I

| Perfluorocarbon | Concentration (Vol.) | Area | Response Factor[1] |
| --- | --- | --- | --- |
| Series A | | | |
| F—decalin | 7.59 ppm | 276,529 | 36,433 |
| F—dimethyladamantane | 6.75 ppm | 695,777 | 103,078 |
| Series B | | | |
| F—decalin | 7.82 ppm | 312,008 | 39,898 |
| 1-hydropentadecafluoro tricyclo [5.2.1.0$^{2,6}$] decane | 7.88 ppm | 470,494 | 59,707 |
| F—dimethyladamantane | 8.50 ppm | 877,753 | 103,265 |
| F—tetramethyladamantane | 9.70 ppm | 26,162 | 2,697 |
| 50/50 (wt.) mixture of F—dimethyladamantane and F—trimethylbicyclononane | 7.88 ppm | 655,842 | 83,229 |
| F—tricyclo [5.2.1.0$^{2,6}$] decane, 65/35 exo/endo isomer mixture | 7.78 ppm | 606,327 | 77,934 |
| F—adamantane | 6.60 ppm | 241,856 | 36,644 |
| Series C | | | |
| F—decalin | 495 ppb | 32,013 | 64,700 |
| F—1-methyladamantane | 465 ppb | 44,445 | 95,600 |
| F—dimethyladamantane | 515 ppb | 69,227 | 134,000 |
| F—tricyclo [5.2.1.0.$^{2,6}$] decane 65/35 exo/endo isomer mixture | 487 ppb | 63,769 | 130,900 |

[1]Response factor = area/concentration

EXAMPLE 2

Water dilutions of the perfluorocarbons listed in Table II below were prepared in field brine obtained from a petroleum reservoir, using isopropanol as a cosolvent, to provide mixtures ranging from $10^{-9}$ to $10^{-14}$ (v/v), i.e., from 1 part per billion to 100 parts per trillion by volume. The detection limits were then determined, using a Varian 3000 gas chromatograph equipped with a Graphpac AT-1000 column and an electron capture detector operated at 300° C. The carrier gas was nitrogen and $Ni^{63}$ was the detector ionization source. The results indicate the very low concentrations at which the perfluorocarbons are detectable. The results were in good agreement with those obtained on the same concentrations of the perfluorocarbons in laboratory grade water. The F-decalin result is shown for comparison although outside the present invention (F-decalin will not survive a catalytic cleanup procedure prior to EC detection).

TABLE II

| Perfluorocarbon[1] | Detection Limit (v/v) | Retention Time (min.) |
|---|---|---|
| F—decalin | $10^{-12}$ | 16.4, 16.9 |
| F—tricyclo [5.2.1.0.$^{2,6}$] decane | $10^{-12}$ | 8.5, 11.0 |
| 1-hydropentadecafluoro tricyclo [5.2.1.0.$^{2,6}$] decane | $10^{-12}$ | 14.6, 16.0 |
| F—bicyclodecane | $10^{-12}$ | 19.1 |
| F—dimethyladamantane | $10^{-11}$ | 17.1, 17.6 |

[1]Major component. The material tested is actually a mixture of various isomers and byproducts.

It is claimed:

1. A tracing method comprising the steps of (1) incorporating a tracer compound into a material or a fluid medium in order to identify the source or distribution of the material or to define the flow pattern of the medium, (2) permitting distribution of the material or flow of the fluid medium, (3) collecting a sample of the material or fluid medium, and (4) analyzing the sample for the presence of the tracer compound, wherein said tracer compound is a perfluorinated $C_9$–$C_{18}$ polycyclic hydrocarbon containing at least two bridgehead carbon atoms linked through a bridge containing at least one carbon atom.

2. The tracing method of claim 1 wherein the tracer compound is F-dimethyladamantane.

3. The tracing method of claim 1 wherein the tracer compound is F-tricyclo[5.2.1.0.$^{2,6}$]decane.

4. The tracing method of claim 1 wherein the tracer compound is F-1-methyladamantane.

5. The tracing method of claim 1 wherein the tracer compound is a mixture of the exo and endo isomers of F-tricyclo[5.2.1.0.$^{2,6}$]decane.

6. The tracing method of claim 1 wherein the tracer compound is 1-hydropentadecafluorotricyclo[5.2.1.0.$^{2,6}$]decane.

7. The tracing method of claim 1 wherein the sample in step (4) is analyzed by electron capture gas chromatography.

8. The tracing method of claim 1 wherein the sample is catalytically treated prior to analysis to remove contaminants.

9. The tracing method of claim 1 wherein the tracer compound is a mixture of an F-alkyladamantane and an F-alkylbicyclononane.

10. The tracing method of claim 9 wherein the F-alkyladamantane is F-dimethyladamantane and the F-alkylbicyclononane is F-trimethylbicyclononane.

* * * * *